United States Patent
Scoggan

(10) Patent No.: US 6,441,003 B1
(45) Date of Patent: Aug. 27, 2002

(54) PROCESS FOR THE APPLICATION OF SYSTEMIC PESTICIDES TO ASEXUAL PLANT PROPAGULES

(75) Inventor: Allen C. Scoggan, Kearney, MO (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/678,604

(22) Filed: Oct. 4, 2000

(51) Int. Cl.[7] ................. A61K 31/44; A01N 43/40; A01N 25/00
(52) U.S. Cl. ................. 514/336; 424/405; 424/5.5; 424/6; 424/DIG. 3
(58) Field of Search ................. 514/336; 424/405; 47/5.5, 6, DIG. 3

(56) References Cited

U.S. PATENT DOCUMENTS

| | | | |
|---|---|---|---|
| 4,291,497 A | 9/1981 | Manankov | 47/58 |
| 4,356,934 A | 11/1982 | Knake | 221/96 |
| 4,596,206 A | 6/1986 | Berge et al. | 118/303 |
| 4,994,487 A | 2/1991 | Haglund | 514/476 |
| 5,112,849 A * | 5/1992 | Staub et al. | 514/427 |
| 5,527,366 A | 6/1996 | Mazurkiewicz | 47/58 |
| 5,575,224 A | 11/1996 | Rogers | 111/118 |
| 5,965,597 A * | 10/1999 | Colliot et al. | 514/404 |

FOREIGN PATENT DOCUMENTS

| | | |
|---|---|---|
| JP | 61254501 | * 11/1986 |
| JP | 03251504 | * 11/1991 |

\* cited by examiner

*Primary Examiner*—Alton Pryor
(74) *Attorney, Agent, or Firm*—Joseph C. Gil

(57) ABSTRACT

The field of this invention is the application of systemic pesticides. More particularly, this invention pertains to an improved process for the internal placement of systemic insecticides, fungicides, acaricides or nematicides into asexual plant propagules, such as tubers, corms, bulbs, stolons, rhizomes, and stems.

4 Claims, No Drawings

PROCESS FOR THE APPLICATION OF SYSTEMIC PESTICIDES TO ASEXUAL PLANT PROPAGULES

TECHNICAL FIELD OF THE INVENTION

The field of this invention is the application of systemic pesticides. More particularly, this invention pertains to an improved process for the internal placement of systemic insecticides, fungicides, acaricides or nematicides into asexual plant propagules, such as tubers, corms, bulbs, stolons, rhizomes, and stems.

BACKGROUND OF THE INVENTION

Systemic pesticides, commonly referred to as systemics, are chemicals which are toxic to pests when ingested, and which are readily absorbed by plants and diffused throughout the plants in their sap streams. Systemics are typically introduced into plants either by application to the leaves of the plants, or to the root systems thereof. When insects feed on plants which have been impregnated with systemics, they ingest the systemics and are poisoned thereby, provided the concentrations in the sap streams are maintained at levels sufficiently high to be lethal.

Various devices and systems for the application of systemics to plants, seeds, and soil, have been developed in the art. U.S. Pat. No. 5,527,366 discloses a method of applying an herbicide to plants which includes delivering a liquid herbicide solution to the plant foliage in a high pressure jet stream to physically disrupt the surface of the foliage. U.S. Pat. No. 4,291,497 describes a method of introducing a chemical agent into plants by spraying or dipping the plant organs into the agent and allowing the agent to penetrate the plant system. U.S. Pat. Nos. 4,994,487 and 5,575,224 disclose a device for injecting a liquid pesticide (fungicide and herbicide, respectively) into the soil adjacent to the root system of plants. U.S. Pat. No. 4,356,934 discloses a seed treatment method which includes spraying of an emulsion containing an insecticide, fungicide or bactericide, onto the seed prior to planting. U.S. Pat. No. 4,596,206 discloses an apparatus for treatment of seeds with a liquid insecticide-fungicide, prior to planting.

A disadvantage of the known methods of applying insecticides to plants is the potential exposure to humans resulting from handling the treated plants.

An advantage of the process of the present invention is the application of the systemic insecticide, fungicide, acaricide or nematicide to the asexual propagules of plants so that it is absorbed by the root systems of the plants, and is isolated from direct contact with the air, soil, water and humans.

BRIEF SUMMARY OF THE INVENTION

The present invention provides an improved process for applying systemic pesticides to plants wherein the improvement comprises incorporating the pesticide internally into an asexual propagule of the plant. The systemic pesticides include systemic insecticides, systemic fungicides, systemic acaricides and systemic nematicides. Many such systemic pesticides are commercially available such as imidacloprid (available from Bayer Corporation under the Admire, Confidor, Gaucho, Merit, Premier, Premise and Provado names), fenamiphos (available from Bayer Corporation under the Nemacur name) and triadimefon (available from Bayer Corporation under the Bayleton name). Additional commercially available systemic pesticides are described in the Farm Chemicals Handbook '99, vol. 85. The asexual plant propagules include the plant tubers, corms, bulbs, stolons, rhizomes, and stems.

DETAILED DESCRIPTION OF THE INVENTION

The present invention provides a process for application of a systemic pesticide to plants. Further, the present invention includes internal placement of the systemic in the plants. In particular, the systemic is placed inside of an asexual plant propagule and the systemic is thereby absorbed by the shoots and foliage growing from the propagule.

The systemic pesticide includes known insecticides, fungicides, acaricides or nematicides. In a preferred embodiment, the insecticide is imidacloprid. The asexual plant propagules include the plant tubers, corms, bulbs, stolons, rhizomes, and stems. Insertion of the systemic pesticide into the asexual plant propagule may be accomplished by hand or by various automated injection devices known in the art. For example, U.S. Pat. No. 4,011,685 discloses a plant injection device which comprises an injection-type needle. The needle portion of the device may be inserted into the plant either by applying force, or by drilling a hole in the plant and inserting the needle therein. U.S. Pat. No. 4,899,488 describes a spray nozzle-type tool for internal application of a liquid agent to plant life.

In an embodiment of the invention, the systemic pesticide is a formulation which contains a known insecticide, fungicide, acaricide or nematicide as an active ingredient. In a preferred embodiment, the formulation includes imidacloprid as the insecticidal active ingredient. In addition to the active ingredient, the formulation may also include an adjuvant.

As is known in the art, an adjuvant is used in a formulation to aid the operation or improve the effectiveness of the pesticide. As is known in the art, the term "adjuvant" includes such materials, as wetting agents, spreaders, emulsifiers, dispersing agents, foaming adjuvants, foam suppressants, penetrants, thickeners, antifreeze agents, correctives, fillers and carriers. A spray adjuvant may contain one or more surfactants, solvents, solubilizers, buffering agents, and stickers needed to formulate a specific type adjuvant. Suitable adjuvants are known and described, for example, in FARM CHEMICALS HANDBOOK '99 and in A GUIDE TO AGRICULTURAL SPRAY ADJUVANTS used in the United States, $5^{th}$ Edition, Thomson, 1998.

The invention if further illustrated but is not intended to be limited by the following examples in which all parts and percentages are by weight unless otherwise specified.

EXAMPLE

Comparison of Insecticide Injected Seed Pieces to Surface-treated Seed Pieces, in-furrow Treatments, and Foliar Spray Treatments For the seed piece injection treatments, each seed piece was drilled with a 5/16" drill to a depth of approximately 20 mm. The appropriate insecticide formulation, a 2.5 granular (GR) or a 240 flowable (FS) was introduced into the drilled hole. The 240 FS formulation was diluted with water to achieve 0.5 ml of formulation per seed piece. The composition of the insecticide formulations is shown in Table 1.

TABLE 1

Ingredients:

Formulation: Imidacloprid 2.5 GR

| Imidacloprid 75 | Active ingredient (75% active) | 3.33 wt. % |
| Dipropylene glycol | Deactivator | 12.00 wt. % |
| Agsorb Granules | Base clay granules | 84.67 wt. % |

Formulation: Imidacloprid 240 FS

| Imidacloprid Technical | Active ingredient (100% active) | 21.40 wt. % |
| Morwet D-425 | Dispersant | 2.00 wt. % |
| EO/PO Block Copolymer | Surfactant, wetting agent | 2.00 wt. % |
| Proxel GXL | Bactericide | 0.50 wt. % |
| Rhodopol 50 MD | Thickener | 0.18 wt. % |
| Glycerine | Antifreeze agent | 10.00 wt. % |
| Water (Deionized) | Carrier | 63.92 wt. % |

The hole was then covered with a "plug" which was cut from untreated tubers with an 11/32" leather punch. The treated seed pieces were allowed to suberize for several hours, and then were hand planted with the "plug" inserted to prevent leakage.

The surface seed treatment was applied by using a finger-plunger atomizing sprayer to spray the appropriate insecticide dosage. The insecticide was diluted with water to 10 ml of total spray per 12-seed-piece batch. One-half of the volume was applied to a surface of the seed piece, the seed pieces were then turned over, and the other half of the insecticide was applied to the opposite surface of the seed piece. The seed pieces were planted and covered.

The in-furrow treatment was applied by opening the 10 inch of furrow, and applying the insecticide by either sprinkling the granules into the furrow out of a coin envelope, or by spraying it into the furrow with a flat fan nozzle turned parallel with the furrow to make an in-furrow spray band of about 2 inches wide. The seed pieces were then planted, and covered.

Untreated seed pieces were also planted as control plots.

No phytotoxicity was seen from any treatment.

Data was first collected 67 days after the seeds were planted. On this date, both adult insects and larvae were present. An average of 4 adults and 3 small larvae per plant were present in the untreated control plots. All of the insecticide treatments were providing excellent control, although a trace of feeding damage was present in the foliar spray treatments.

By the second observation date, 97 days after the seeds were planted, a heavy infestation had developed, with some adults and many larvae present on the control plots. The three seed piece injection treatments were still very effective, with only a few larvae present in the 2.5 GR 0.03 g/meter treatment, and the 240 FS 0.006 and 0.003 g/meter treatments were still virtually larvae-free. The surface-applied seed treatment was still showing food plant protection, but was allowing larvae survival with an average of about 10 larvae per plant. The in-furrow treatments were still showing plant protection, but were obviously starting to fail with about 5 to 50 larvae present per plant. The foliar spray treatments had failed, with many larvae present and considerable defoliation. By the final observation date, 110 days after the seeds were planted, all the untreated plants in the control plots and those plants which received in-furrow and foliar treatments were virtually completely defoliated. The plants receiving injected seed piece treatments were still being protected from insects, and hundreds of dead and moribund adults could be seen under the plants and in the furrows. The plants which received the surface seed piece treatment were showing noticeably more defoliation, but the insecticide continued to work to kill both adult insects and larvae.

The injected seed piece treatments were clearly superior, and were still providing insect mortality and plant protection for 110 days after planting. The in-furrow treatments gave good protection for approximately 90 days. The foliar treatments only gave protection for about 45 days. Results of the tests are presented in Table 2.

TABLE 2

| Formulation ID | Rate g/m | Treatment Type | % Plant leaves Destroyed (by Colorado Potato beetles) | | |
|---|---|---|---|---|---|
| | | | 67 d | 97 d | 110 d |
| Untreated | — | — | 2.08 | 40.0 | 100.0 |
| Imidacloprid 2.5 GR | 0.03 | In-Furrow | 0.00 | 25.0 | 100.0 |
| Imidacloprid 240 FS | 0.03 | In-Furrow | 0.00 | 18.7 | 100.0 |
| Imidacloprid 2.5 GR | 0.03 | Seed Inj. | 0.00 | 0.05 | 21.2 |
| Imidacloprid 240 FS | 0.006 | Seed Inj. | 0.00 | 0.05 | 13.7 |
| Imidacloprid 240 FS | 0.003 | Seed Inj. | 0.00 | 5.00 | 43.7 |
| Imidacloprid 240 FS | 50 | Foliar | 0.01 | 30.0 | 100.0 |
| Imidacloprid* 240 FS | 50 | Foliar | 0.01 | 47.5 | 100.0 |
| Imidacloprid+ 240 FS | 50 | Foliar | 0.01 | 32.5 | 100.0 |
| Imidacloprid* 240 FS | 50 | Foliar | 0.00 | 38.7 | 100.0 |

*Insecticidal formulation contained 0.25% of a wetting agent.
+Insecticidal formulation contained 0.0625% of a wetting agent.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An improved process for applying a systemic pesticide to asexual plants, wherein the improvement comprises injecting the systemic internally into an asexual propagule of the plant.

2. The process of claim 1 wherein the systemic pesticide is selected from the group consisting of insecticides, fungicides, acaricides and nematicides.

3. The process of claim 1 wherein said asexual propagule is selected from the group consisting of tubers, corms, bulbs, stolons, rhizomes, and stems.

4. The process of claim 1 wherein the systemic pesticide comprises an active ingredient and at least one adjuvant.

* * * * *